United States Patent
Yoneyama et al.

(10) Patent No.: US 11,510,650 B2
(45) Date of Patent: Nov. 29, 2022

(54) ULTRASOUND DIAGNOSIS APPARATUS, MEDICAL IMAGE DIAGNOSIS APPARATUS, AND COMPUTER PROGRAM PRODUCT

(71) Applicant: Toshiba Medical Systems Corporation, Otawara (JP)

(72) Inventors: Naoki Yoneyama, Yaita (JP); Takatoshi Okumura, Yaita (JP); Naoyuki Nakazawa, Otawara (JP); Masatoshi Nishino, Otawara (JP); Norihisa Kikuchi, Otawara (JP); Kazutoshi Sadamitsu, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 614 days.

(21) Appl. No.: 15/720,934

(22) Filed: Sep. 29, 2017

(65) Prior Publication Data
US 2018/0092629 A1    Apr. 5, 2018

(30) Foreign Application Priority Data
Sep. 30, 2016    (JP) ............................. JP2016-192884

(51) Int. Cl.
*A61B 8/00* (2006.01)
*A61B 8/06* (2006.01)
*A61B 8/08* (2006.01)

(52) U.S. Cl.
CPC ............... *A61B 8/463* (2013.01); *A61B 8/06* (2013.01); *A61B 8/4427* (2013.01);
(Continued)

(58) Field of Classification Search
CPC ......... A61B 8/463; A61B 8/06; A61B 8/4427; A61B 8/5261; A61B 8/4416; A61B 8/467; A61B 8/5238
See application file for complete search history.

(56) References Cited

U.S. PATENT DOCUMENTS

| 7,038,588 B2 * | 5/2006 | Boone ................ A61B 5/02055 340/573.1 |
| 2003/0007598 A1 * | 1/2003 | Wang .................. A61B 8/5238 378/37 |

(Continued)

FOREIGN PATENT DOCUMENTS

| JP | 2011-167331 | 9/2011 |
| JP | 2014-524083 | 9/2014 |

OTHER PUBLICATIONS

Japanese Office Action dated Aug. 25, 2020 in Japanese Application No. 2016-192884, 6 pgs.

*Primary Examiner* — Bo Joseph Peng
(74) *Attorney, Agent, or Firm* — Oblon, McClelland, Maier & Neustadt, L.L.P.

(57) ABSTRACT

According to one embodiment, an ultrasound diagnosis apparatus includes an image processing circuit and a processing circuit. The image processing circuit generates an ultrasound image. The processing circuit receives a medical image acquired by another medical image diagnosis apparatus, and aligns the ultrasound image and the medical image. The processing circuit has a function of recognizing identification information held by the medical image when the ultrasound image and the medical image are displayed side by side on a display. The processing circuit also has a function of retrieving diagnostic protocol information corresponding to the identification information and displaying it on the display, and a function of performing examinations and processes based on the diagnostic protocol information displayed.

11 Claims, 7 Drawing Sheets

(52) U.S. Cl.
CPC .......... *A61B 8/5261* (2013.01); *A61B 8/4416* (2013.01); *A61B 8/467* (2013.01); *A61B 8/5238* (2013.01)

(56) References Cited

U.S. PATENT DOCUMENTS

| | | | | |
|---|---|---|---|---|
| 2003/0069503 | A1* | 4/2003 | Matsui | A61B 8/465 600/437 |
| 2007/0244393 | A1* | 10/2007 | Oshiki | A61B 5/02007 600/463 |
| 2012/0063661 | A1* | 3/2012 | Nishimura | A61B 8/00 382/131 |
| 2013/0158397 | A1* | 6/2013 | K. | A61B 8/4472 600/437 |
| 2013/0190600 | A1* | 7/2013 | Gupta | A61B 8/0866 600/410 |

* cited by examiner

FIG.4

| B MODE |
|---|
| DISTANCE MEASUREMENT |
| STILL IMAGE SAVING |
| B MODE (COMPRESSION) |
| STILL IMAGE SAVING |
| COLOR MODE |
| STILL IMAGE SAVING |

FIG.6

| |
|---|
| B MODE |
| DISTANCE MEASUREMENT |
| STILL IMAGE SAVING |
| COLOR MODE |
| STILL IMAGE SAVING |
| CONTRAST AGENT MODE |
| MOVING IMAGE SAVING ARTERIAL PHASE |
| MOVING IMAGE SAVING PORTAL VEIN PHASE (LATE VASCULAR PHASE) |
| MOVING IMAGE SAVING LATE PHASE (SUBSTANTIAL PHASE) |
| PUNCTURE MODE (BIOPSY GUIDE DISPLAY) |
| MOVING IMAGE SAVING (IMAGES CAPTURED DURING PUNCTURING) |

ULTRASOUND DIAGNOSIS APPARATUS, MEDICAL IMAGE DIAGNOSIS APPARATUS, AND COMPUTER PROGRAM PRODUCT

CROSS-REFERENCE TO RELATED APPLICATION

This application is based on and claims the benefit of priority from Japanese Patent Application No. 2016-192884, filed on Sep. 30, 2016; the entire contents of which are incorporated herein by reference.

FIELD

Embodiments described herein relate generally to an ultrasound diagnosis apparatus, a medical image diagnosis apparatus, and a computer program product.

BACKGROUND

Medical treatment has been performed with the support of a medical image diagnosis apparatus based on the technological progress of modality (medical image diagnosis apparatuses). In addition, various medical image diagnosis apparatuses are used when a doctor conducts a diagnosis or when the disease state of a patient is determined. However, upon determining the disease state using a medical image diagnosis apparatus, for example, when the disease state to be determined is of a severe disease such as cancer, in many cases, the disease state is not determined only by information obtained from one medical image diagnosis apparatus. This is to more accurately determine the disease state. In this case, a plurality of medical image diagnosis apparatuses are used.

Among the medical image diagnosis apparatuses is an ultrasound diagnosis apparatus. The ultrasound diagnosis apparatus can noninvasively examine the internal structure and blood flow state of a patient. For example, the ultrasound diagnosis apparatus is used as one medical image diagnosis apparatus for determining a disease state relating to the abdomen and extremities. For example, after a medical image illustrating internal information of a patient is acquired by using an X-ray CT apparatus, the disease state of the patient may be determined based on the medical image displayed on the ultrasound diagnosis apparatus together with an ultrasound image.

When the X-ray CT apparatus is used first and then the ultrasound diagnosis apparatus is used as above, the doctor looks at the medical image acquired by the X-ray CT apparatus and marks a part or an area that bothers him/her. This mark indicates a part or an area desired to be the object of an examination conducted by using the ultrasound diagnosis apparatus. Then, the marked part or area is examined with the ultrasound diagnosis apparatus to collect information leading to the final determination of the disease state.

When an examination is performed using the ultrasound diagnosis apparatus, if a medical image acquired by the X-ray CT apparatus and an ultrasound image acquired by the ultrasound diagnosis apparatus are displayed on the same screen, the mark on the medical image is also displayed. Accordingly, the examination is performed more accurately.

In order to determine the disease state of a patient, the part or area marked on the medical image is examined with a medical image diagnosis apparatus different from the one which has acquired the medical image. On this occasion, for example, in the case of an experienced operator, he/she can accurately perform the examination necessary for determining the disease state based on the mark displayed on the screen. However, if the operator is not experienced in the examination, he/she may not be able to acquire as much information as necessary to make the final determination of the disease state compared to the experienced operator. Even if the examination is performed reliably, the final determination of the disease state is made by individual doctors. As a result, the determination may vary depending on the doctors.

BRIEF DESCRIPTION OF THE DRAWINGS

FIG. 4 is an explanatory diagram illustrating an example of diagnostic protocol information indicating the flow of examinations performed when a benign liver tumor is suspected;

FIG. 6 is an explanatory diagram illustrating an example of diagnostic protocol information indicating the flow of examinations performed when a malignant liver tumor is suspected.

DETAILED DESCRIPTION

Figure 1:
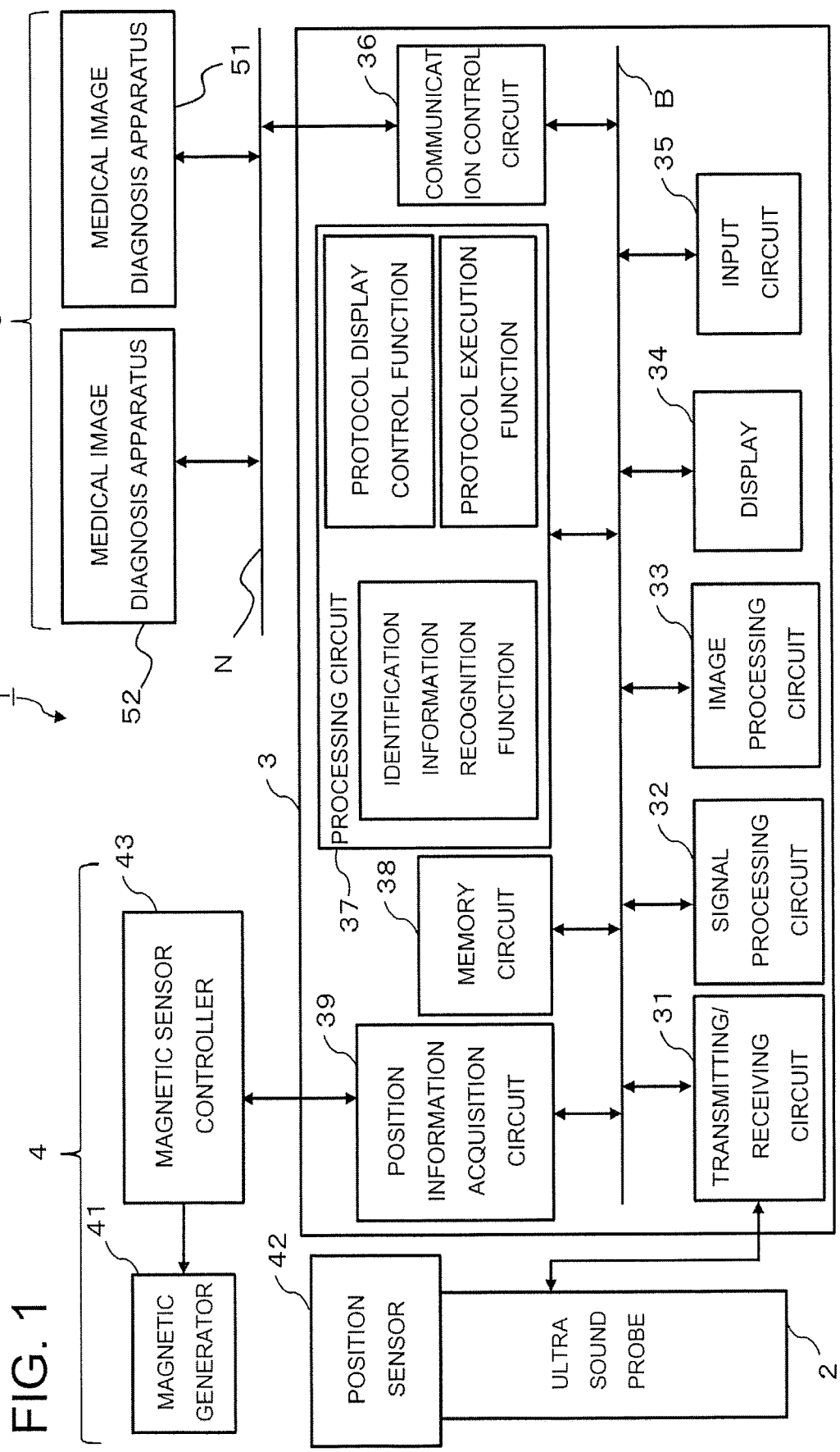
FIG. 1 is a block diagram illustrating the overall configuration of an ultrasound diagnosis apparatus according to a first embodiment.

In general, according to one embodiment, an ultrasound diagnosis apparatus includes an image processing circuit and a processing circuit. The image processing circuit generates an ultrasound image based on a reflected signal received by a transmitting/receiving circuit that transmits a drive signal for driving ultrasound transducers of an ultrasound probe and receive the reflected signal. The processing circuit receives a medical image acquired by another medical image diagnosis apparatus, and displays the ultrasound image and the medical image. The processing circuit has a function of recognizing identification information held by the medical image, and a function of displaying diagnostic protocol information corresponding to the identification information.

Referring now to the drawings, illustrative embodiments are described in detail.

First Embodiment

[Configuration of Ultrasound Diagnosis Apparatus]

FIG. 1 is a block diagram illustrating the overall configuration of an ultrasound diagnosis apparatus 1 according to a first embodiment. As illustrated in FIG. 1, the ultrasound diagnosis apparatus 1 includes an ultrasound probe 2 that transmits/receives ultrasound waves (transmitted and received waves) to/from a patient, and a main body 3 to which the ultrasound probe 2 is detachably connected. In the first embodiment, the ultrasound diagnosis apparatus is described as an example of an apparatus that performs examinations and processes based on identification information attached to a medical image.

The ultrasound probe 2 is used in a state where its distal end surface is in contact with the surface of a patient, and transmits/receives ultrasound waves. The ultrasound probe 2 incorporates a plurality of ultrasound transducers, which are arrayed, for example, one-dimensionally on the distal end surface. The ultrasound probe 2 transmits ultrasound waves into the patient through each of the ultrasound transducers to scan a scan area, and receives reflected waves from the patient as echo signals. Examples of the scan include various types of scans such as B mode scan and Doppler mode scan.

Besides, examples of the ultrasound probe 2 include a sector scan probe, a linear scan probe, a convex scan probe and the like, one of which is arbitrarily selected according to a diagnosis site. The ultrasound transducers need not necessarily be arranged in a one-dimensional array, but may be arrayed two-dimensionally such that volume data can be acquired in real time. In the case of obtaining a pseudo three-dimensional stereoscopic image in this way, a probe for three-dimensional scanning is used as the ultrasound probe 2. Examples of the probe for three-dimensional scanning include a two-dimensional array probe and a mechanical probe.

The main body 3 includes a transmitting/receiving circuit 31 configured to transmit a drive signal to the ultrasound probe 2 and receive a reflection signal from the ultrasound probe 2, a signal processing circuit 32 configured to process the reflection signal, an image processing circuit 33 configured to generate an ultrasound image, a display 34 configured to display various images, and an input circuit 35 configured to receive an input signal as being operated by an operator such as an examiner. The main body 3 further includes a communication control circuit 36 configured to control the transmission/reception of signals to/from other medical image diagnosis apparatuses 51 and 52 (hereinafter, collectively referred to as "medical image diagnosis apparatus 5" unless each of them is specifically referred to), that connected a communication network N a processing circuit 37 configured to control each part, a memory circuit 38 configured to store, for example, a medical image diagnosis support program, and a position information acquisition circuit 39 configured to figure out the position of the ultrasound probe 2 These circuits are connected to a bus B, and can exchange various signals.

Under the control of the processing circuit 37, the transmitting/receiving circuit 31 generates a drive signal for causing the ultrasound probe 2 to generate ultrasound waves, i.e., an electric pulse signal (hereinafter referred to as "drive pulse") to be applied to each of the piezoelectric transducers, and transmits the drive pulse to the ultrasound probe 2. The transmitting/receiving circuit 31 includes circuits (not illustrated) such as a reference pulse generating circuit, a delay control circuit, a drive pulse generating circuit, and the like, and each circuit performs the functions mentioned above. In addition, the transmitting/receiving circuit 31 receives a reflection signal, i.e., echo signal, from the ultrasound probe 2. The transmitting/receiving circuit 31 performs phasing addition on the received signal, and outputs the resultant signal to the signal processing circuit 32.

The signal processing circuit 32 generates various types of data using the received signal from the ultrasound probe 2 fed by the transmitting/receiving circuit 31, and outputs the data to the image processing circuit 33 and the processing circuit 37. The signal processing circuit 32 includes, for example, a B mode processing circuit (or Bc mode processing circuit), a Doppler mode processing circuit, a color Doppler mode processing circuit, and the like (not illustrated). The B mode processing circuit visualizes the amplitude information of the received signal, and generates data based on a B mode signal. The Doppler mode processing circuit extracts Doppler shift frequency component from the received signal, and applies fast Fourier transform (FFT) or the like thereto, thereby generating Doppler signal data of blood flow information. The color Doppler mode processing circuit visualizes the blood flow information based on the received signal, and generates data based on a color Doppler mode signal.

The image processing circuit 33 generates two-dimensional or three-dimensional ultrasound images of the scan area based on the data supplied from the signal processing circuit 32. For example, the image processing circuit 33 generates volume data related to the scan area from the supplied data. Then, from the volume data generated, the image processing circuit 33 generates data of a two-dimensional ultrasound image by multi-planar reconstruction (MPR) and data of a three-dimensional ultrasound image by volume rendering. The image processing circuit 33 outputs the two-dimensional or three-dimensional ultrasound image to the display 34. Examples of the ultrasound image include a B mode image, a Doppler mode image, a color Doppler mode image, an M mode image, and the like.

The display 34 displays various images such as an ultrasound image generated by the image processing circuit 33 and an operation screen (e.g., graphical user interface (GUI) configured to receive various instructions from the operator) under the control of the processing circuit 37. As the display 34, for example, a liquid crystal display (LCD), an organic electroluminescence (EL) display, or the like can be used.

Incidentally, the display 34 of the embodiment includes, in addition to a display as a main monitor, a monitor provided separately from the main monitor (hereinafter referred to as "sub monitor" for convenience). The sub monitor is configured to display, for example, switches and content that cannot be displayed on the main monitor because of the display area of the main monitor, diagnostic protocol information (described later), and the like.

Further, in the embodiment, the display 34 is described as one constituent element of the ultrasound diagnosis apparatus 1; however, it is not so limited. The display 34 need not necessarily be a constituent element of the ultrasound diagnosis apparatus 1, but may be, for example, a display separate from the ultrasound diagnosis apparatus 1.

The input circuit 35 receives various input operations made by the operator to provide, for example, an instruction to capture an image, display an image or switch images, designation of the mode, various settings, and the like. For example, GUI, an input device such as buttons, a keyboard, a trackball, or the like can be used as the input circuit 35.

The communication control circuit 36 enables the ultrasound diagnosis apparatus 1 to communicate with the other medical image diagnosis apparatuses (modalities), an image server, a work station, and the like via the communication network N. Information and medical images exchanged between the communication control circuit 36 and the medical image diagnosis apparatus 5 via the communication network N may be in conformity with any standards such as digital imaging and communication in medicine (DICOM) and the like.

The communication network N connects the ultrasound diagnosis apparatus 1 and the medical image diagnosis apparatus 5, and enables them to exchange, for example, medical image information. Examples of the communication network N include a local area network (LAN) and the Internet.

The processing circuit 37 comprehensively controls each part of the ultrasound diagnosis apparatus 1. For example, the processing circuit 37 aligns an ultrasound image generated by the image processing circuit 33 and a medical image acquired from the medical image diagnosis apparatus 5, and displays the images side by side on the display 34. The processing circuit 37 has a function of recognizing identification information of each medical image, a function of retrieving diagnostic protocol information corresponding to the identification information and displaying it on the display, and a function of performing an examination process based on the diagnostic protocol information displayed.

The "medical image" is an image generated by the medical image diagnosis apparatus 5. In the following description, "medical image" may be equated with "medical image data" as appropriate.

In the medical image, for example, information for identifying a disease state (hereinafter referred to as "identification information") is added to a part or an area that bothers a doctor or the like who viewed the medical image. The identification information refers to information that can serve as a basis for determining the disease state when an examination is performed with the ultrasound diagnosis apparatus. That is, there are a plurality of types of identification information with respect to each disease state, and their meanings are each defined. The identification information need not necessarily indicate a disease state, but may indicate some other meaning or may be defined by a relationship with the examination or a site to be examined.

The identification information may be displayed in any mode as long as a person, who performs an examination by using another medical image diagnosis apparatus (ultrasound diagnosis apparatus) to determine the disease state with reference to the medical image, can identify the disease state. For example, the identification information may be displayed as a mark, comments, words, letters or characters, numerical information, or the like. They may be used singly or in combination to form the identification information. Further, the identification information may be attached to the medical image, embedded in the medical image, or stored as additional information in the header part of DICOM.

The term "diagnostic protocol information" as used herein refers to information indicating procedures and examination items determined according to the clinical practice guidelines defined for each disease state. That is, the diagnostic protocol information serves as a guide for the examiner to perform examinations and processes. The diagnostic protocol information is associated with the identification information and stored in the memory circuit 38. Diagnostic protocol information corresponding to the identification information is retrieved from the memory circuit 38 and displayed. The examiner can acquire information necessary for determining the disease state by performing examinations and processes according to the diagnostic protocol information. Incidentally, the diagnostic protocol information is determined in advance according to the clinical practice guidelines; however, it may be changed in each medical institution.

In the first embodiment, the processing circuit 37 of the ultrasound diagnosis apparatus 1 is configured to perform various examinations and processes based on the diagnostic protocol information. However, for example, the medical image diagnosis support program may be used to implement the functions of the processing circuit 37. In this case, the medical image diagnosis support program is loaded into the processing circuit 37 and executed. Thereby, the processing circuit 37 recognizes identification information, displays the diagnostic protocol information, and performs examinations and processes based on the diagnostic protocol information through the functions defined by the medical image diagnosis support program.

Besides, the medical image diagnosis support program may be loaded into the processing circuit 37 of the ultrasound diagnosis apparatus 1 and executed to thereby implement at least one function of the signal processing circuit 32, the image processing circuit 33, or the position information acquisition circuit 39 (described later), and the other configuration may be constituted by an independent circuit.

The memory circuit 38 is formed of, for example, a semiconductor or a magnetic disk, and stores programs to be executed by the processing circuit 37, data, identification information, and the like. The memory circuit 38 also stores diagnostic protocol information defined for each clinical practice guideline in association with the identification information.

The position information acquisition circuit 39 acquires the position information of the ultrasound probe 2. Specifically, the position information acquisition circuit 39 acquires the position information of the ultrasound probe 2 measured by a position measuring system 4 arranged outside the main body 3. The position measuring system 4 includes a magnetic generator 41, a position sensor 42, and a magnetic sensor controller 43.

The magnetic generator 41 is located around the ultrasound diagnosis apparatus 1 and generates magnetism. The position of the magnetic generator 41 serves as the position of the origin. The position sensor 42 is provided to the ultrasound probe 2. The three-dimensional position and inclination of the ultrasound probe 2 in the real space (position information) are measured based on a signal from the position sensor 42 which receives a change in the magnetic field generated by the magnetic generator 41. The magnetic sensor controller 43 controls the generation of magnetism in the magnetic generator 41, and sends the position information of the ultrasound probe 2 measured to the position information acquisition circuit 39.

For example, the signal processing circuit 32, the image processing circuit 33, and the like can be realized by a program that causes a processor to execute a program stored in a predetermined memory, the memory circuit 38, or the like. The term "processor" as used herein refers to a circuit such as, for example, a dedicated or general central processing unit (CPU) arithmetic circuit (circuitry), an application specific integrated circuit (ASIC), a programmable logic device including a simple programmable logic device (SPLD) and a complex programmable logic device (CPLD), a field programmable gate array (FPGA), or the like.

The processor reads out, for example, a program stored in a recording circuit or directly incorporated in the circuit of the processor and execute it, thereby realizing the functions. The recording circuit for storing the program may be provided for each processor or may be a storage that stores a program corresponding to the functions of the signal processing circuit 32 illustrated in FIG. 1. Further, the configuration of the memory circuit 38 illustrated in FIG. 1 may be adopted to store the program. The memory circuit 38 is formed of a storage device like a semiconductor memory and a magnetic disk such as a general random access memory (RAM) and a hard disc drive (HDD).

The medical image diagnosis apparatus 5 is used to acquire a medical image of a target patient before determining the disease state with the ultrasound diagnosis apparatus 1. Examples of the medical image diagnosis apparatus 5 include an X-ray computed tomography (CT) apparatus, a magnetic resonance imaging (MRI) apparatus, and the like. The medical image diagnosis apparatus 5 is connected to the communication network N. The medical image diagnosis apparatus 5 sends a medical image accompanied with the above-described identification information to the ultrasound diagnosis apparatus 1, which is also connected to the communication network N, via the communication network N.

[Operation]

Figure 2:
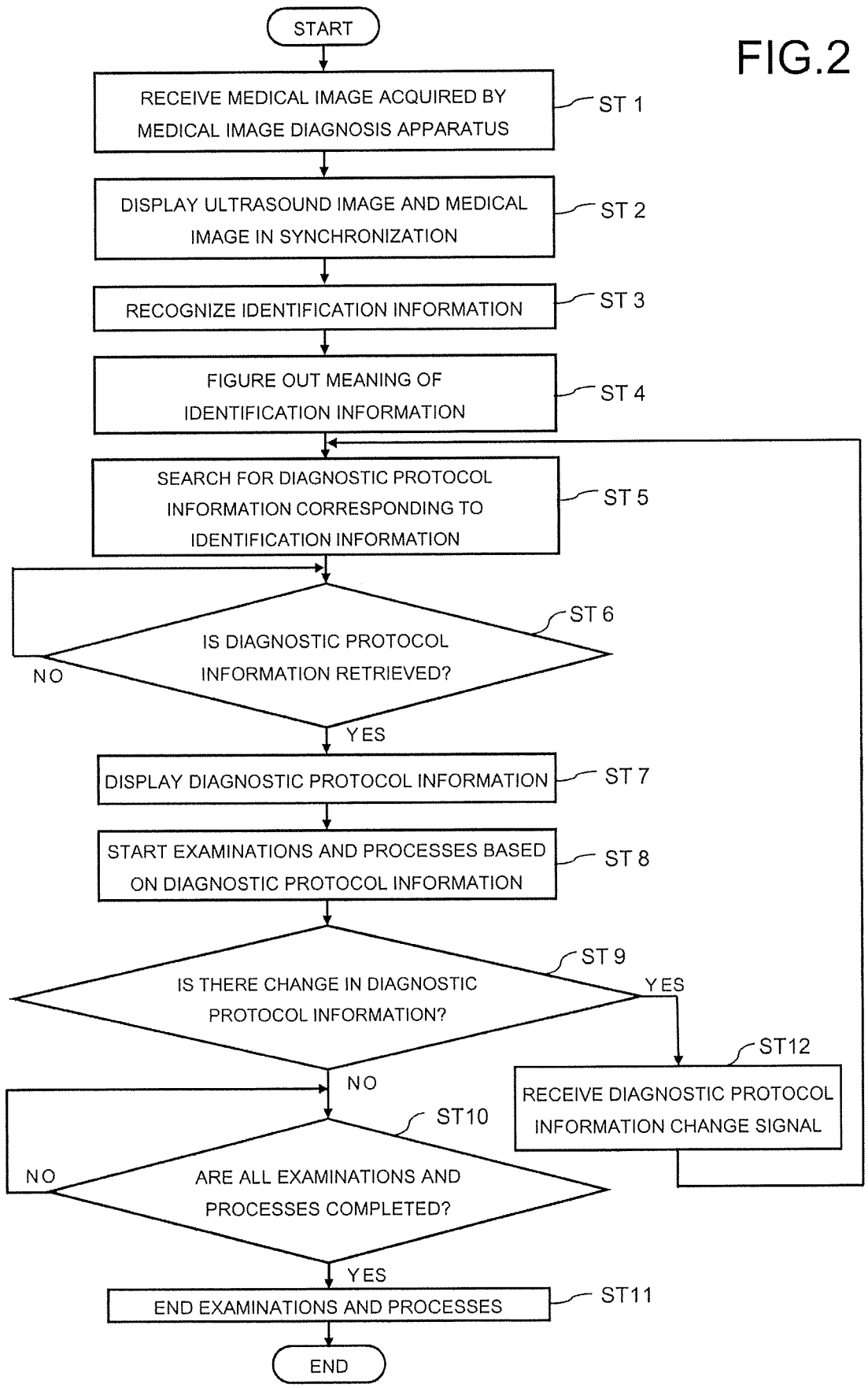
FIG. 2 is a flowchart illustrating the operation of determining the disease state in an embodiment.

Next, with reference to FIGS. 2 to 6, a description is given of the operation of determining the disease state by using the ultrasound diagnosis apparatus 1. FIG. 2 is a flowchart illustrating the operation of determining the disease state in the embodiment. Although not specifically mentioned, the identification information is recognized by the identification information recognition function of the processing circuit 37 in the following example. Besides, diagnostic protocol information is displayed based on the identification information and the diagnostic protocol information by the protocol display control function of the processing circuit 37. Examinations and processes are performed according to the diagnostic protocol information by the protocol execution function of the processing circuit 37.

First, the medical image diagnosis apparatus 5 acquires a medical image illustrating internal information of a patient. A doctor or the like views the medical image, and marks a part or an area that bothers him/her. This mark indicates a part or an area desired to be the object of the examination conducted by using the ultrasound diagnosis apparatus, and serves as identification information. For example, a part where a benign tumor is suspected is marked with a circle, and a part where a malignant tumor is suspected is marked with a cross. In this manner, what the identification information means is determined in advance. The doctor or the like attaches the identification information representing a prescribed meaning to the data of the medical image.

In the embodiment, an example is described in which the ultrasound diagnosis apparatus 1 acquires the data of the medical image having the identification information from the medical image diagnosis apparatus 5; however, it is not so limited. It suffices if the ultrasound diagnosis apparatus 1 can acquire medical image data having identification information. Therefore, for example, a doctor or the like may attach identification information to the data of a medical image by using a work station (not illustrated) connected to the communication network N such that the ultrasound diagnosis apparatus 1 can acquire the medical image. In other words, the medical image accompanied with the identification information need not necessarily be acquired from the medical image diagnosis apparatus 5.

The data of the medical image, to which the identification information is attached by the doctor or the like, is transmitted from the medical image diagnosis apparatus 5 to the ultrasound diagnosis apparatus 1 via the communication network N. With regard to the transmission of the data of the medical image to the ultrasound diagnosis apparatus 1, the data of the medical image may be stored in advance in an apparatus such as the medical image diagnosis apparatus 5 or an image server connected to the communication network N. While the data of the medical image is described as being transmitted from the medical image diagnosis apparatus 5 to the ultrasound diagnosis apparatus 1 via the communication network N, for example, it may be stored in a portable storage medium and delivered to the ultrasound diagnosis apparatus 1.

The ultrasound diagnosis apparatus 1 receives the medical image acquired by the medical image diagnosis apparatus 5 (ST1). As described above, the medical image received by the ultrasound diagnosis apparatus 1 has identification information attached by the doctor or the like who views the medical image.

An examiner, i.e., a doctor, who operates the ultrasound diagnosis apparatus 1, brings the ultrasound probe 2 into contact with the patient to be examined and displays an ultrasound image on the display 34. The patient to be examined is a patient who is the object of the medical image acquired by the medical image diagnosis apparatus 5. The examiner displays the medical image together with the ultrasound image on the display 34.

As described above, the ultrasound probe 2 of the embodiment is provided with the position sensor 42, and the position of the ultrasound probe 2 can be found out. The ultrasound image and the medical image are aligned based on the position information of the ultrasound probe 2 thus obtained and the position information of the data of the medical image, and displayed on the same screen in synchronization with each other (ST2). Thus, the identification information indicated in the medical image is illustrated in the ultrasound image.

In the following, a description is given of a case where the identification information indicates that a benign tumor is suspected and a case where the identification information indicates that a malignant tumor is suspected. The liver is cited as an example of the affected part marked with the identification information.

Figure 3:
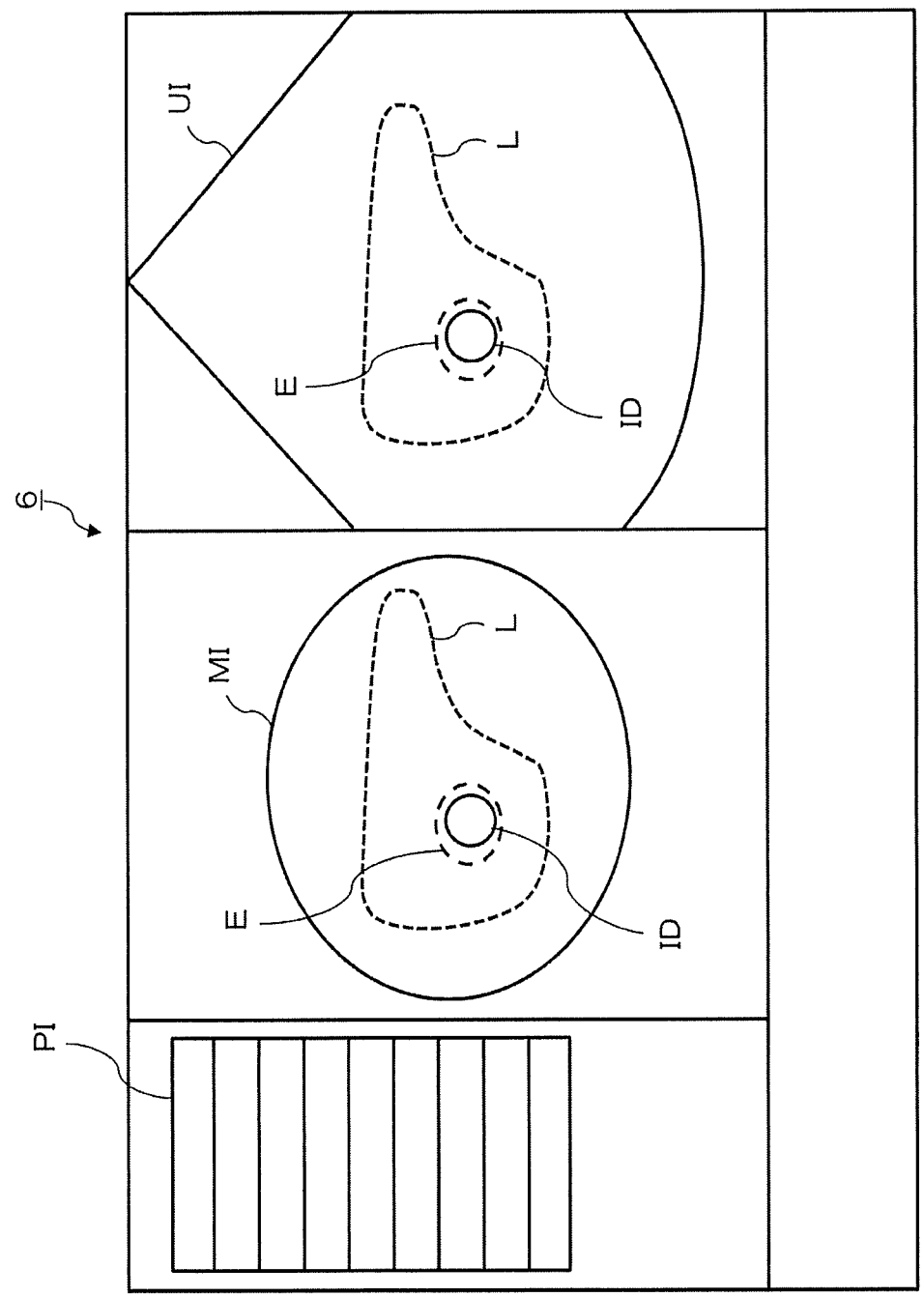
FIG. 3 is an example of images displayed when an examination is performed to determine the disease state, and is a diagram illustrating a case where a benign liver tumor is suspected.

FIG. 3 is an example of images displayed on the display 34 of the ultrasound diagnosis apparatus 1 when an examination is performed to determine the disease state. FIG. 3 illustrates an example of a screen in a case where a benign liver tumor is suspected. A display screen 6 is roughly divided into three areas in the horizontal direction of the display screen 6. A medical image MI is displayed in the center of the display screen 6, In FIG. 3, the liver L as the affected part is indicated by a dotted line. In addition, a lesion present area E is indicated by a broken line as an area where a lesion may be present in the liver L.

The doctor is required to make a final determination on the disease state in the lesion present area E by using the ultrasound diagnosis apparatus 1. Accordingly, the lesion present area E is indicated by identification information ID. In FIG. 3, the identification information ID is represented by a solid circle indicating a case where a benign liver tumor is suspected.

Since the medical image MI and an ultrasound image UI have already been aligned, the identification information ID illustrated in the medical image MI is also illustrated at the same position in the ultrasound image UI displayed on the right side. The examiner performs examinations and processes using the ultrasound diagnosis apparatus 1 to determine the disease state of the area indicated by the identification information ID.

At the left end of the display screen 6, there is an area for displaying diagnostic protocol information PI (described later). Although the diagnostic protocol information PI is described as being displayed together with the medical image MT and the ultrasound image UI on the display screen 6 of the ultrasound diagnosis apparatus 1, it is not so limited. For example, if the display 34 is formed of two monitors such as a main monitor and a sub monitor, the medical image MI and the ultrasound image UI may be displayed on the main monitor while the diagnostic protocol information PI may be displayed on the sub monitor.

The processing circuit 37 of the ultrasound diagnosis apparatus 1 recognizes the identification information ID indicated in the medical image MI (ST3). Specifically, for example, the shape of the identification information ID is analyzed to recognize the shape (pattern), or the identification information ID is recognized based on the position information of the identification information ID in the medical image MI. In the embodiment, the processing circuit 37 figures out that the identification information ID is illustrated in a part of the liver illustrated in FIG. 3. Further, the processing circuit 37 figures out the meaning of the identification information ID with the solid circle recognized (ST4).

In the example of FIG. 3, a solid circle is illustrated in a part of the liver. The solid circle serves as the identification information ID indicating that a benign liver tumor is suspected in the liver. Thus, the processing circuit 37 determines that "a benign liver tumor is suspected" from the identification information ID represented by the solid circle.

The processing circuit 37 searches the memory circuit 38 for the corresponding diagnostic protocol information PI based on the identification information ID (ST5). Since the identification information ID indicates that a "benign liver tumor" is suspected, the diagnostic protocol information PI relating to a benign liver tumor is to be retrieved. The memory circuit 38 stores the identification information ID and the diagnostic protocol information PI in association with each other.

Then, it is determined that whether the diagnostic protocol information PI relating to a benign liver tumor has been retrieved from the memory circuit 38 (ST6). If the diagnostic protocol information PI has not been retrieved (NO in ST6), the retrieval is waited for. If the diagnostic protocol information PI has been retrieved (YES in ST6), the diagnostic protocol information PI is displayed on the display 34 (ST7). In the example of FIG. 3, the diagnostic protocol information PI is displayed at the left end of the display screen 6. The diagnostic protocol information PI may be controlled to be displayed on the sub monitor as described above.

FIG. 4 is an explanatory diagram illustrating an example of the diagnostic protocol information PI indicating the flow of examinations performed when a benign liver tumor is suspected. That is, FIG. 4 illustrates the diagnostic protocol information PI displayed at the left end of the display screen 6. In FIG. 4, the flow of examinations to be performed according to the diagnostic protocol information PI to determine the disease state is illustrated from the top to the bottom. By performing the examinations according to the diagnostic protocol information PI, information necessary for determining the disease state can be acquired. In addition, by performing the examinations indicated in order in the diagnostic protocol information PI, all the required examinations can be performed.

Incidentally, the title is not indicated in the diagnostic protocol information PI illustrated in FIG. 4. The title may be, for example, "benign liver tumor". In this manner, in a case, for example, where it is not preferable if the patient can see the title, the title may not be displayed. Meanwhile, when the diagnostic protocol information PI includes title information, naturally, the title can be displayed.

The examiner starts an examination process based on the diagnostic protocol information PI displayed (ST8). That is, the examiner performs examinations and processes in order according to each item indicated in the diagnostic protocol information PI. In the following, with reference to FIG. 4 illustrating an example of the diagnostic protocol information PI, the examinations performed to determine the disease state when a benign liver tumor is suspected are described in order.

First, a "B mode" examination is carried out. Next, "distance measurement" is performed. The "distance measurement" refers to a process of measuring the size and the aspect ratio of a tumor. For example, in the case of a malignant liver tumor, it is found that the measured value indicates a slightly irregular shape.

When one examination is completed and the next examination is started, the processing circuit 37 recognizes the transition from one examination to the next examination based on, for example, the diagnostic protocol information PI. In this case, the processing circuit 37 displays the completed examination on the display screen 6 in such a manner as to clearly indicate the fact that the examination is completed. For example, the display of the completed examination may be highlighted, inactive, or changed in color.

When one of the examinations and processes, which need to be performed in order, is skipped, i.e., if the processing circuit 37 determines that a selected examination or a process is not the next one defined by the diagnostic protocol information PT, for example, the notification thereof may be provided by voice or the like. Further, for example, the display of each examination may be provided with a check box such that the examiner may check it each time the examination is completed. In this case, the next examination or process cannot be performed unless the check box is checked. In addition, when all the processes are completed, the notification thereof may be provided.

Besides, it is cumbersome to perform each of the examinations and processes according to the diagnostic protocol information PI by operating the input circuit 35 of the ultrasound diagnosis apparatus 1. In the embodiment, the examinations to be performed are defined in order in the diagnostic protocol information PT. Therefore, for example, a setting may be made such that the operation to start and end the examination and make a transition to the next examination or process can be performed by only pressing one button.

Upon completion of the "distance measurement", the process moves to "still image saving". The "still image saving" refers to a process of saving a still image displayed on the display screen 6. The processing circuit 37 receives an input operation from the examiner and stores the still image displayed on the display screen 6 in, for example, the memory circuit 38.

After the "still image saving" process, the examiner further performs a "B mode (compression)" examination. The "B mode (compression)" examination refers to an examination performed by pressing the probe against a relevant portion. Since the benign liver tumor is soft, it is crushed if the liver is compressed. Therefore, whether it is a benign liver tumor or not can be determined by compressing the liver while "B mode" imaging is being carried out. Then, while the liver is being compressed, the "still image saving" process is performed to store a still image of the liver being compressed.

"Color mode" refers to a process of displaying the ultrasound image UI acquired by the ultrasound diagnosis apparatus 1 in color. In the case of a benign liver tumor, the blood vessel may not be formed in the tumor as well. Therefore, when the ultrasound image of the liver is displayed in the "color mode", the ultrasound image UI is displayed with the color of the blood vessel. In other words, by the process of displaying the image in the "color mode", whether there is a blood flow is displayed. Thus, it can be determined whether the liver tumor is benign. Upon receipt of an operation for selecting the "color mode" from the examiner, the processing circuit 37 instructs the image processing circuit 33 to generate an image to be displayed in the "color mode". The "color mode" image generated by the image processing circuit 33 is displayed on the display screen 6. Then, the aforementioned "still image saving" process is performed again.

Figure 5:
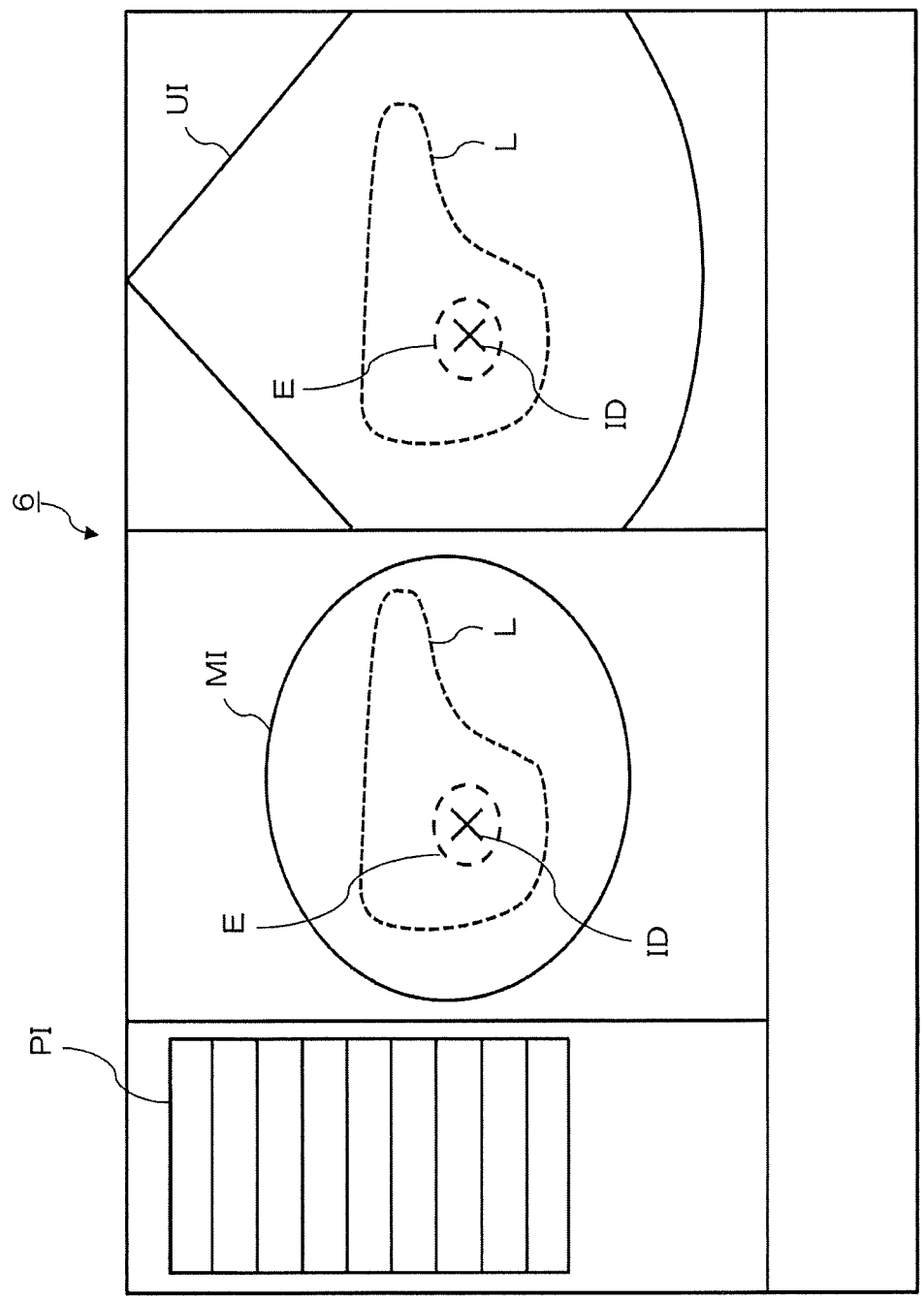
FIG. 5 is an example of images displayed when an examination is performed to determine the disease state, and is a diagram illustrating a case where a malignant liver tumor is suspected.

A case where a benign liver tumor is suspected has been described above. In the following, a case where a malignant liver tumor is suspected is described. FIG. 5 is an example of images displayed on the display 34 when an examination is performed to determine the disease state. FIG. 5 illustrates an example of a screen in a case where a malignant liver tumor is suspected. FIG. 6 is an explanatory diagram illustrating an example of the diagnostic protocol information PI indicating the flow of examinations performed when a malignant liver tumor is suspected.

As illustrated in FIG. 5, the identification information ID illustrated in the lesion present area E of the medical image MI is also illustrated in the ultrasound image UT. In the lesion present area E of both the images, the identification information ID is indicated by a cross mark. The identification information ID indicated by a cross mark represents a case where a malignant liver tumor is suspected. Basically, the operation of performing examinations and processes is similar to that in a case where a benign liver tumor is suspected described with reference to FIG. 2 except items of examinations and processes.

FIG. 6 illustrates the diagnostic protocol information PI indicating the flow of examinations and processes required when a malignant liver tumor is suspected. The flow from "B mode" to "color mode" and "still image saving" is basically the same as that in the case of a benign liver tumor; however, different examinations and processes are performed thereafter.

Incidentally, in this case, the "B mode (compression)" examination and the "still image saving" processes are not performed. This is because a malignant liver tumor is already suspected, and there is no need to examine the softness of the liver tumor by compressing the liver to check whether it is a benign liver tumor.

After the completion of the "color mode" process and the "still image saving" process, a "contrast agent mode" examination is performed. Since thin blood vessels may pass through the malignant liver tumor, an examination is performed by using a contrast agent to observe the blood vessels.

After the contrast agent is injected into the patient, the process of "moving image saving" related to three phases of "arterial phase", "portal vein phase (late vascular phase)" and "late phase (substantial phase)" is performed. The "moving image saving" refers to the process of storing data of ultrasound images in the memory circuit 38 with the lapse of time. This process is performed in response to an operation for storing a moving image received by the processing circuit 37. In addition, the "moving image saving" process may be triggered when the "moving image saving" process is selected and ultrasound waves are transmitted from the ultrasound probe 2 to the patient, or upon recognizing the completion of injection of the contrast agent. In any of these cases, whether it is a malignant liver tumor or not is determined based on whether the contrast agent appears in the moving image or how it appears.

The examinations and processes performed when a malignant liver tumor is suspected end up by conducting a "puncture mode (biopsy guide display)" examination and "moving image saving (images captured during puncturing)" process.

The operation of examinations and processes using the diagnostic protocol information PI has been described by taking a case where a benign liver tumor is suspected and a case where a malignant liver tumor is suspected as examples.

As described above, the examiner performs examinations and processes in the order indicated in the diagnostic protocol information PI. However, in the course of the examinations and processes, the examiner may have doubts as to the disease state indicated by the identification information ID. The identification information ID is attached to the medical image MI acquired by the medical image diagnosis apparatus 5 before the examinations and processes are performed with the ultrasound diagnosis apparatus 1 at the discretion of a doctor or the like who viewed the image MI. Therefore, there may be a case where it is found that the examinations and processes performed based on the identification information ID (the diagnostic protocol information PI corresponding thereto) attached to the medical image MI are not appropriate through the course of the examinations and processes using the ultrasound diagnosis apparatus 1.

In such a case, the examiner performs a change process at any stage of the examinations and processes to change the diagnostic protocol information PI such that he/she can start examinations based on the diagnostic protocol information PI corresponding to the disease state that he/she suspects.

Therefore, while the examinations and processes based on the diagnostic protocol information PI are being performed, the processing circuit 37 monitors whether to receive a signal instructing to change the diagnostic protocol information PI from the examiner through the input circuit 35 (ST9).

As a result, if an instruction to change the diagnostic protocol information PI is not received from the examiner (NO in ST9) while the examinations and processes are being performed based on the diagnostic protocol information PI currently displayed on the display 34, the examinations and processes based on the current diagnostic protocol information PI are continued.

The processing circuit 37 monitors whether all the examinations and processes indicated in the diagnostic protocol information PI have been completed (ST10). If not (NO in ST10), the processing circuit 37 continues monitoring. If all the examinations are completed (YES in ST10), the examination and the process using the ultrasound diagnosis apparatus 1 end (ST11). This enables the examiner to acquire various information on the disease state. Thus, it is possible to make a final determination on the disease state.

On the other hand, if the examiner has doubts as to the presumed disease state in the course of the examinations and processes based on the diagnostic protocol information PI displayed on the display 34, the correct disease state cannot be determined with the examinations and processes base on the current diagnostic protocol information PI. Therefore, it is necessary to carry out examinations and processes required to determine a new disease state suspected by the examiner. Accordingly, the examiner changes the current diagnostic protocol information PI to new one.

More specifically, for example, when the examiner operates a menu button as a part of the input circuit 35, a screen for the current examinations and processes is changed to a screen for temporarily interrupting the examinations and processes currently being performed to receive an operation for selecting interruption from the examiner. Thereafter, a screen for selecting new diagnostic protocol information PI is displayed. For example, the processing circuit 37 determines that the diagnostic protocol information PI is to be changed in response to the display of the screen for selecting new diagnostic protocol information PI (YES in ST9).

The examiner selects new diagnostic protocol information PI that is displayed on the screen for selecting new diagnostic protocol information PI. For example, new diagnostic protocol information PI is selected from a plurality of pieces of diagnostic protocol information, and is intended to be for examinations to determine the disease state that the examiner suspects. The processing circuit 37 receives, from the input circuit 35, a signal indicating that new diagnostic protocol information PI is selected (ST12).

When new diagnostic protocol information PI is selected, the process returns to step ST5, and the corresponding diagnostic protocol information PI is retrieved from the memory circuit 38. The processing circuit 37 displays the new diagnostic protocol information PI on the display 34. The examiner performs examinations and processes based on the diagnostic protocol information PI newly displayed. The examinations and processes are performed in the same manner as described above.

As described above, in the ultrasound diagnosis apparatus and the medical image diagnosis support program of the embodiment, diagnostic protocol information according to the clinical practice guidelines is set in advance. When an examination is performed to determine the disease state of a patient, the diagnostic protocol information can be displayed correspondingly to the disease state suspected based on information held by a medical image. With the ultrasound diagnosis apparatus and the medical image diagnosis support program of the embodiment, the examiner is led to perform examinations based on the diagnostic protocol information as a guide. Thus, all the necessary examinations can be performed.

Since the examiner conduct examinations according to the diagnostic protocol information as a guide, the experiences and methods of a plurality of examiners can be standardized. Moreover, the omission of examination can be prevented. As a result, more definite diagnosis can be achieved. Further, information on the point of interest can be relayed without omission among a plurality of medical image diagnosis apparatuses used for definite diagnosis.

Second Embodiment

In the following, a second embodiment is described. In the second embodiment, like reference numerals designate like elements as those described in the first embodiment, and the same description is not repeated.

In the first embodiment, an ultrasound diagnosis apparatus has been described as an example of an apparatus for performing examinations and processes based on identification information attached to a medical image. In the second embodiment, an example is described in which a medical image diagnosis apparatus is used as an apparatus for performing examinations and processes to determine a disease state. In the following, an X-ray CT apparatus is described as an example of the medical image diagnosis apparatus.

[Configuration of Medical Image Diagnosis Apparatus]

Figure 7:
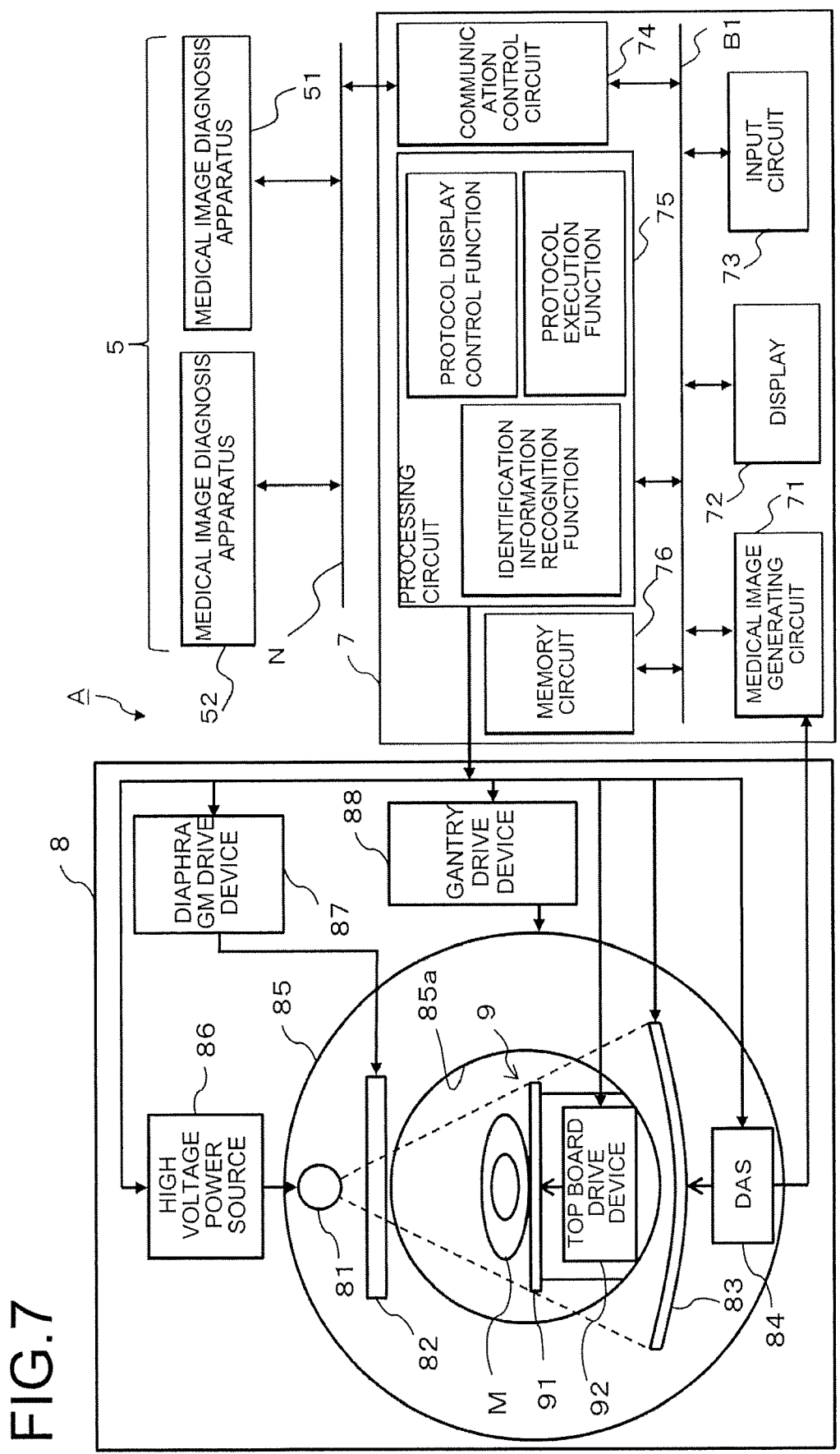
FIG. 7 is a block diagram illustrating the overall configuration of a medical image diagnosis apparatus according to a second embodiment.

FIG. 7 is a block diagram illustrating the overall configuration of a medical image diagnosis apparatus A according to the second embodiment. The medical image diagnosis apparatus A includes a controller 7 configured to control the medical image diagnosis apparatus A, a medical image acquisition device 8 installed in, for example, an examination room and configured to acquire internal information of a patient M to be examined, and a bed 9 on which the patient M is placed.

The controller 7 includes a medical image generating circuit 71, a display 72, an input circuit 73, a communication control circuit 74, a processing circuit 75, and a memory circuit 76. The medical image generating circuit 71, the display 72, the input circuit 73, the communication control circuit 74, the processing circuit 75, and the memory circuit 76 are connected via a bus B1.

The medical image generating circuit 71 receives data transmitted from DAS 84 (described later), and generates a medical image that represents the internal information of the patient M by using the data. The medical image generated is transmitted to the processing circuit 75, for example.

The display 72 displays various images such as those generated by the medical image generating circuit 71 (hereinafter, referred to as "first medical image"), and operation screens (e.g., graphical user interface (GUI) configured to receive various instructions from the operator) under the control of the processing circuit 75. As the display 72, for example, LCD, an organic EL display, or the like can be used.

Incidentally, the display 72 of the embodiment may include, in addition to a display as a main monitor, a sub monitor provided separately from the main monitor. The sub monitor is configured to display, for example, switches and content that cannot be displayed on the main monitor because of the display area of the main monitor, diagnostic protocol information, or the like.

The input circuit 73 receives various input operations made by the operator to provide, for example, an instruction to capture an image, display an image or switch images, various settings, and the like. For example, GUI, an input device such as buttons, a keyboard, a trackball, or the like can be used as the input circuit 73.

The communication control circuit 74 enables the medical image diagnosis apparatus A to communicate with the other medical image diagnosis apparatus 5, an image server, a work station, and the like via a communication network N. Information and medical images exchanged between the communication control circuit 74 and the medical image diagnosis apparatus 5 via the communication network N may be in conformity with any standards such as DICOM.

The communication network N connects the medical image diagnosis apparatus A and the medical image diagnosis apparatus 5, and enables them to exchange, for example, medical image information. Examples of the communication network N include LAN and the Internet.

The processing circuit 75 comprehensively controls each part of the medical image diagnosis apparatus A. For example, the processing circuit 75 aligns the first medical image generated by the medical image generating circuit 71 and a medical image generated by the medical image diagnosis apparatus 5 (hereinafter referred to as "second medical image"), and displays both the medical images side by side on the display 72. The processing circuit 75 has a function of recognizing identification information of the second medical image, a function of acquiring diagnostic protocol information corresponding to the identification information and displaying it on the display, and a function of performing an examination process based on the diagnostic protocol information displayed.

Identification information ID is added to the second medical image generated by the medical image diagnosis apparatus 5 by a doctor or the like who viewed the second medical image. The identification information ID refers to information that can serve as a basis for determining the disease state when an examination is performed with the medical image diagnosis apparatus A. The second medical image acquired by the medical image diagnosis apparatus A from the medical image diagnosis apparatus 5 through the communication control circuit 74 and displayed on the display 72 is accompanied with the identification information ID. The identification information ID is reflected on the first medical image generated by the medical image generating circuit 71 in the medical image diagnosis apparatus A after the alignment.

In the second embodiment, the processing circuit 75 of the medical image diagnosis apparatus A is configured to perform various examinations and processes based on the diagnostic protocol information PI; however, it is not so limited. For example, a medical image diagnosis support program may be used to implement the functions of the processing circuit 75. In this case, the medical image diagnosis support program is loaded into the controller 7 of the medical image diagnosis apparatus A and executed. Thereby, the general-purpose processor of the medical image diagnosis apparatus A recognizes identification information, displays the diagnostic protocol information, and performs examinations and processes based on the diagnostic protocol information through the functions defined by the medical image diagnosis support program.

Besides, the medical image diagnosis support program may be loaded into the processing circuit 75 of the medical image diagnosis apparatus A and executed to thereby implement the functions of the medical image generating circuit 71 described above, and the other configuration may be constituted by an independent circuit.

The memory circuit 76 is formed of, for example, a semiconductor or a magnetic disk, and stores programs to be executed by the processing circuit 75, data, identification information, and the like. The memory circuit 76 also stores diagnostic protocol information defined for each clinical practice guideline in association with the identification information.

The medical image diagnosis apparatus A is provided with the medical image acquisition device 8 controlled by the controller 7. The medical image acquisition device 8 includes an X-ray tube (X-ray source) 81 as an X-ray generator, a diaphragm 82, an X-ray detector 83 as an X-ray detection device, a data acquisition system (DAS) 84, a gantry (mount) 85, a high voltage power source 86, a diaphragm drive device 87, a gantry drive device 88, and a top board drive device 92.

The X-ray tube 81 generates X-rays by accelerating electrons with a tube voltage supplied from the high-voltage power source 86 and allowing them to collide with a metal target, and irradiates the X-rays toward the X-ray detector 83. The X-rays irradiated by the X-ray tube 81 form fan beam X-rays and cone beam X-rays.

The diaphragm 82 is driven by the diaphragm drive device 87 to adjust the irradiation range of the X-rays irradiated from the X-ray tube 81 in the slice direction. With this, the irradiation range of the X-rays in the slice direction can be changed to an arbitrary orientation.

The X-ray detector 83 detects X-rays irradiated from the X-ray tube 81 and transmitted through the patient M. The X-ray detector 83 may be, for example, a one-dimensional array detector having an array of detection elements arranged in the channel direction, i.e., one in the column (slice) direction. Alternatively, the X-ray detector 83 may be a two-dimensional array detector having a matrix of detection elements, i.e., a plurality of them in the channel direction and the column direction.

The DAS 84 amplifies the signal of the transmission data detected by each of X-ray detection elements constituting the X-ray detector 83, and converts it into a digital signal. The data output from the DAS 84 is sent to the medical image generating circuit 71 of the controller 7.

The gantry 85 irradiates the patient M with X-rays and detects X-rays having passed the patient M. Thus, the gantry 85 has a tunnel-shaped opening 85a in the center thereof to allow the patient M to enter and exit it. The gantry 85 holds the X-ray tube 81, the diaphragm 82, the X-ray detector 83 and the DAS 84 in one.

The X-ray tube 81 and the X-ray detector 83 are arranged in positions opposed to each other in the gantry 85. The gantry 85 holds the X-ray tube 81, the diaphragm 82, the X-ray detector 83 and the DAS 84 in one, and rotates around the patient M in the center of rotation thereof to perform photography.

Under the control of the controller 7, the high voltage power source 86 supplies power required for the X-ray irradiation of the X-ray tube 81 to the X-ray tube 81.

The diaphragm drive device 87 has a mechanism for adjusting the irradiation range of X-rays in the slice direction in the diaphragm 82. The diaphragm drive device 87 adjusts the irradiation range under the control of the controller 7.

Under the control of the controller 7, the gantry drive device 88 rotates the gantry 85 around the patient M place on a top board 91 in the opening 85a of the gantry 85 while maintaining the positional relationship of the devices held in the gantry 85.

The bed 9 includes the top board 91 and the top board drive device 92. When the internal information of the patient M is acquired using the medical image diagnosis apparatus A, i.e., when images thereof are captured, the patient M is directly in contact with the top board 91. When being in direct contact with the top board 91, the patient M need not necessarily lie thereon. The top board drive device 92 is located under the top board 91, and moves the top board 91, on which the patient M is placed, up and down along the height direction under the control of the controller 7 along with the progress of photography in the gantry 85.

In the medical image diagnosis apparatus A, when the patient M is photographed, the top board drive device 92 may drive the top board 91 to enter or exit the gantry 85, or the gantry 85 may be moved such that the top board 91 enter and exit the gantry 85.

[Operation]

The internal configuration of the medical image diagnosis apparatus A has been described above. In the second embodiment, an examiner, i.e., a doctor, collects data for determining the disease state using the medical image diagnosis apparatus A and derives the final determination of the disease state.

The medical image diagnosis apparatus A generates the first medical image. The identification information ID indicated in the second medical image acquired by the medical image diagnosis apparatus 5 is reflected on the first medical image generated. The examiner performs examinations and processes for the patient M according to the diagnostic protocol information PI corresponding to the identification information ID. The examinations and processes based on the diagnostic protocol information PI are performed in the same manner as described above in the first embodiment by taking the ultrasound diagnosis apparatus 1 as an example except that the medical image diagnosis apparatus is used instead of the ultrasound diagnosis apparatus 1.

As described above, in the medical image diagnosis apparatus and the medical image diagnosis support program of the embodiment, diagnostic protocol information according to the clinical practice guidelines is set in advance. When an examination is performed to determine the disease state of a patient, the diagnostic protocol information can be displayed correspondingly to the disease state suspected based on information held by a medical image. With the medical image diagnosis apparatus and the medical image diagnosis support program of the embodiment, the examiner is led to perform examinations based on the diagnostic protocol information as a guide. Thus, all the necessary examinations can be performed.

Since the examiner conduct examinations according to the diagnostic protocol information as a guide, the experiences and methods of a plurality of examiners can be standardized. Moreover, the omission of examination can be prevented. As a result, more definite diagnosis can be achieved. Further, information on the point of interest can be relayed without omission among a plurality of medical image diagnosis apparatuses used for definite diagnosis.

Specific embodiments have been described by way of example, and not by way of limitation. For example, in the first and second embodiments described above, there is one piece of identification information indicated in a medical image or an ultrasound image. However, the number of pieces of identification information indicated in a medical image or the like is not limited to one, and there may be a plurality of pieces of identification information.

In this manner, when a plurality of pieces of identification information are indicated in a medical image or the like, diagnostic protocol information is displayed with respect to each piece of the identification information. In this case, for example, all pieces of the diagnostic protocol information can be displayed in a list. Further, since the examiner performs necessary examinations and processes in order according to each diagnostic protocol information displayed, for example, the pieces of the diagnostic protocol information may be displayed in the order in which the examiner conducts the examinations and processes.

In the embodiments described above, for example, an ultrasound diagnosis apparatus and a medical image diagnosis apparatus (X-ray CT apparatus) are cited as an apparatus for performing examinations and processes to determine a disease state; however, it is not so limited. For example, MRI may be used as an apparatus for performing examinations and processes to determine a disease state based on identification information attached to a medical image acquired by a medical image diagnosis apparatus (X-ray CT apparatus).

The embodiments described above can be implemented in various other forms, and are susceptible to several modifications and variations (omission, substitution, addition, etc.), all coming within the scope of the claims which follow While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising processing circuitry configured to:
    transmit a drive signal for driving ultrasound transducers of an ultrasound probe and receive a reflected signal;
    generate an ultrasound image based on the reflected signal;
    receive a medical image acquired by another medical image diagnosis apparatus and identification information for identifying a disease state determined based on the medical image, and display the ultrasound image and the medical image,
    recognize the identification information held by the medical image, and
    display diagnostic protocol information corresponding to the identification information, the displayed diagnostic protocol information defines properties of one or more ultrasound images to be acquired in association with the identified disease state indicated by the identification information,
    wherein
    the diagnostic protocol information is information indicating procedures and examination items that are performed by an examiner to acquire the one or more ultrasound images corresponding to the identification information, and
    the displayed diagnostic protocol information includes the examination items arranged in an order of execution.

2. The ultrasound diagnosis apparatus of claim 1, further comprising a memory circuit configured to store the diagnostic protocol information in association with the identification information.

3. The ultrasound diagnosis apparatus of claim 1, wherein the ultrasound probe includes a position sensor, and
    the processing circuitry is further configured to align the ultrasound image and the medical image based on position information of the ultrasound probe received from the position sensor.

4. The ultrasound diagnosis apparatus of claim 1, wherein the identification information is formed of at least one of a mark, a letter, a comment, and numerical information.

5. The ultrasound diagnosis apparatus of claim 4, wherein the at least one of the mark, the letter, the comment, and the numerical information is associated with a location on the medical image.

6. The ultrasound diagnosis apparatus of claim 1, wherein the diagnostic protocol information is defined according to clinical practice guidelines.

7. The ultrasound diagnosis apparatus of claim 1, wherein the processing circuitry is further configured to:
    analyze the identification information held by the medical image to determine what the identification information indicates, and
    display the diagnostic protocol information according to the determination result of what the identification information indicates.

8. The ultrasound diagnosis apparatus of claim 1, wherein the identification information held by the medical image is recognized based on a shape or position information of the identification information.

9. The ultrasound diagnosis apparatus of claim 8, further comprising a memory circuit configured to store the diagnostic protocol information in association with the shape or the position information of the identification information.

10. The ultrasound diagnosis apparatus of claim 1, wherein the processing circuitry is further configured to:

recognize a transition of an examination item currently being performed from one examination item to a next examination item based on the diagnostic protocol information;

determine whether a next examination item selected by the examiner is a next one of the examination items defined by the diagnostic protocol information; and provide the examiner with a notification when the next examination item selected by the examiner is not the next one of the examination items defined by the diagnostic protocol information.

11. The ultrasound diagnosis apparatus of claim 1, wherein the processing circuitry is further configured to:

when receiving a signal indicating an instruction to change the diagnostic protocol information from an examiner during execution of the examination items based on the diagnostic protocol information, change from a display screen of current diagnostic protocol information that displays the execution items to be performed by the examiner such that the execution items are arranged in the order of execution to a display screen for selecting new diagnostic protocol information; and when the new diagnostic protocol information is selected by the examiner, display new examination items to be performed by the examiner that are defined by the selected new diagnostic protocol information such that the new examination items are arranged in an order of execution.

\* \* \* \* \*